US012583999B2

(12) United States Patent
Okazawa

(10) Patent No.: US 12,583,999 B2
(45) Date of Patent: Mar. 24, 2026

(54) WATER-ABSORBING RESIN PARTICLES, ABSORBING BODY, AND ABSORBENT ARTICLE

(71) Applicant: SUMITOMO SEIKA CHEMICALS CO., LTD., Kako-gun (JP)

(72) Inventor: Shiho Okazawa, Himeji (JP)

(73) Assignee: SUMITOMO SEIKA CHEMICALS CO., LTD., Kako-gun (JP)

( * ) Notice: Subject to any disclaimer, the term of this patent is extended or adjusted under 35 U.S.C. 154(b) by 539 days.

(21) Appl. No.: 18/254,994

(22) PCT Filed: Nov. 29, 2021

(86) PCT No.: PCT/JP2021/043691
§ 371 (c)(1),
(2) Date: May 30, 2023

(87) PCT Pub. No.: WO2022/118800
PCT Pub. Date: Jun. 9, 2022

(65) Prior Publication Data
US 2024/0110042 A1 Apr. 4, 2024

(30) Foreign Application Priority Data
Dec. 2, 2020 (JP) ................................ 2020-200191

(51) Int. Cl.
*C08K 5/3445* (2006.01)
*A61F 13/53* (2006.01)
(Continued)

(52) U.S. Cl.
CPC ............ *C08K 5/3445* (2013.01); *A61F 13/53* (2013.01); *C08J 3/12* (2013.01); *C08J 3/20* (2013.01); *C08J 3/245* (2013.01)

(58) Field of Classification Search
CPC combination set(s) only.
See application file for complete search history.

(56) References Cited

U.S. PATENT DOCUMENTS

2002/0165288 A1* 11/2002 Frenz ..................... A61L 15/60 521/50
2005/0013865 A1* 1/2005 Nestler .................. A61L 15/60 424/487

(Continued)

FOREIGN PATENT DOCUMENTS

CN 106673215 5/2017
CN 111116817 5/2020

(Continued)

OTHER PUBLICATIONS

International Preliminary Report on Patentability of PCT/JP2021/043691, Jun. 15, 2023, 5 pages.

(Continued)

*Primary Examiner* — Joseph D Anthony
(74) *Attorney, Agent, or Firm* — HSML P.C.

(57) ABSTRACT

The present invention relates to water-absorbing resin particles including: an imidazoline compound represented by Formula (1) below. In Formula (1), R represents a C1-3 alkyl group.

(1)

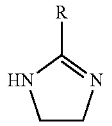

5 Claims, 2 Drawing Sheets

(51) Int. Cl.

| | |
|---|---|
| ***C08J 3/12*** | (2006.01) |
| ***C08J 3/20*** | (2006.01) |
| ***C08J 3/24*** | (2006.01) |

(56) References Cited

U.S. PATENT DOCUMENTS

| | | | | |
|---|---|---|---|---|
| 2005/0145684 | A1* | 7/2005 | Gaeta | B65D 5/2033 229/164 |
| 2005/0176834 | A1* | 8/2005 | Hintz | B32B 27/12 521/50 |
| 2010/0063215 | A1* | 3/2010 | Yano | C08G 65/2663 525/474 |
| 2010/0143495 | A1* | 6/2010 | Hill | A61L 9/01 424/618 |
| 2011/0160398 | A1* | 6/2011 | Bucevschi | A61L 15/60 525/54.1 |
| 2015/0270123 | A1* | 9/2015 | Arata | H01L 21/02068 134/4 |
| 2017/0009113 | A1* | 1/2017 | Itano | C09J 11/04 |
| 2020/0263024 | A1* | 8/2020 | Yamamoto | C08J 3/20 |
| 2022/0023115 | A1* | 1/2022 | Okazawa | C08F 2/32 |
| 2022/0023486 | A1* | 1/2022 | Hama | C08J 3/24 |

FOREIGN PATENT DOCUMENTS

| | | |
|---|---|---|
| JP | 3231881 B | 11/2001 |
| JP | 2015-013992 | 1/2015 |
| JP | 2019-518839 | 7/2019 |
| JP | 2002-510320 | 4/2022 |
| JP | 2022-087997 | 6/2022 |
| WO | 95/010543 | 4/1995 |
| WO | 97/17397 | 5/1997 |
| WO | 99/001427 | 1/1999 |
| WO | 2018/147600 | 8/2018 |

OTHER PUBLICATIONS

The Extended European Search Report issued in EP Application No. 21900553.5, dated Sep. 9, 2024, 5 pages.
International Search Report of PCT/JP2021/043691, Feb. 1, 2022, 2 pages.

* cited by examiner

WATER-ABSORBING RESIN PARTICLES, ABSORBING BODY, AND ABSORBENT ARTICLE

TECHNICAL FIELD

The present invention relates to water-absorbing resin particles, an absorbing body, and an absorbent article.

BACKGROUND ART

Water-absorbing resin particles are used for sanitary materials such as paper diapers and sanitary products, for agricultural and horticultural materials such as water-retaining materials and soil conditioners, and for industrial materials such as water-blocking materials for cables and condensation-preventing materials.

Water-absorbing resin particles generally contain a polymer formed through a polymerization reaction of a monomer having a polymerizable functional group (Patent Literature 1).

CITATION LIST

Patent Literature

[Patent Literature 1] Japanese Patent No. 3231881

SUMMARY OF INVENTION

Technical Problem

In a case where the liquid to be absorbed contains iron, the water-absorbing resin particles are likely to reduce the viscosity of a swollen gel formed after absorbing the liquid over time, and as a result, sufficient liquid-absorbing performance may be unlikely to be maintained. In addition, it is desirable that the water-absorbing resin particles used for diapers and the like have better water absorbency even under no pressure.

One aspect of the present invention is to provide water-absorbing resin particles which have better water absorbency under no pressure and suppress reduction in viscosity over time when swollen with an iron-containing aqueous solution.

Solution to Problem

Water-absorbing resin particles of one aspect of the present invention include: an imidazoline compound represented by Formula (1) below.

[Chem. 1]

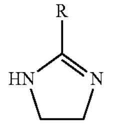

(1)

[In Formula (1), R represents a C1-3 alkyl group.]

One aspect of the present invention relates to an absorbing body: including the above-described water-absorbing resin particles. One aspect of the present invention also relates to an absorbent article including the above-described absorbing body.

Advantageous Effects of Invention

According to the present invention, it is possible to provide water-absorbing resin particles which have better water absorbency under no pressure and suppress reduction in viscosity over time when swollen with an iron-containing aqueous solution.

DESCRIPTION OF EMBODIMENTS

Figure 1:
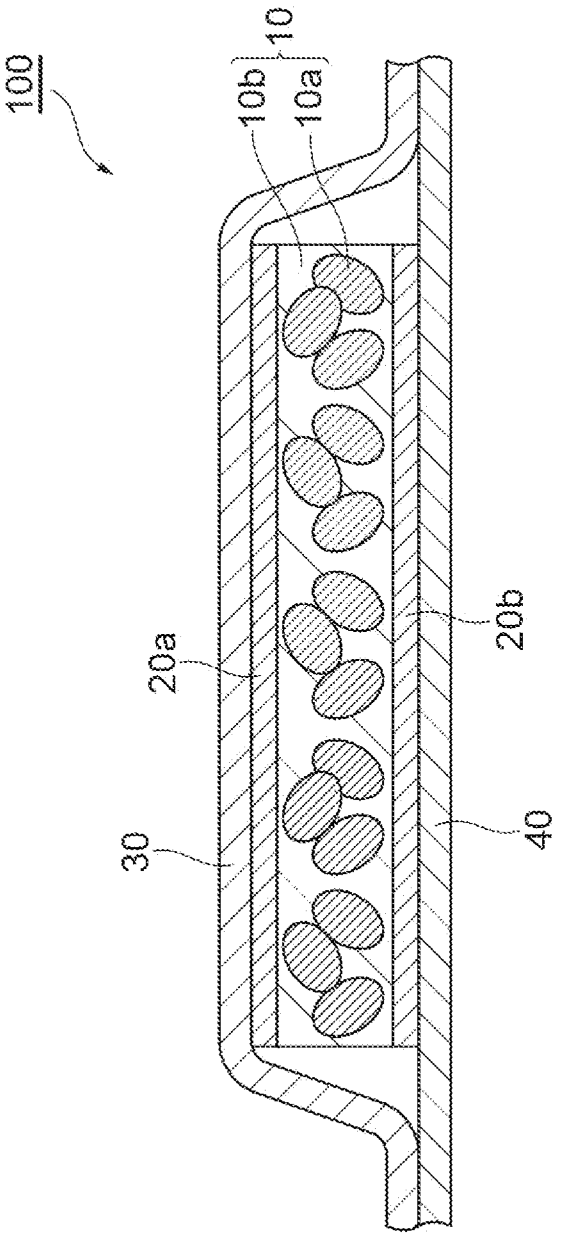
FIG. 1 is a cross-sectional view illustrating one embodiment of an absorbent article.

Hereinafter, embodiments of the present invention will be described in detail. However, the present invention is not limited to the following embodiments, and can be implemented with various modifications within the scope of the gist.

In the present specification, "acryl" and "methacryl" are collectively denoted as "(meth)acryl." "Acrylate" and "methacrylate" are similarly denoted as "(meth)acrylate." In numerical ranges described stepwise in the present specification, an upper limit value or a lower limit value of a numerical range in a certain step can be arbitrarily combined with an upper limit value or a lower limit value of a numerical range in another step. In the numerical ranges described in the present specification, upper limit values or lower limit values of the numerical ranges may be replaced with values shown in examples. "Water solubility" means exhibiting solubility of 5 mass % or more in water at 25° C. Materials exemplified in the present specification may be used alone or in combination of two or more thereof. The content of each component in a composition means a total amount of multiple substances present in the composition unless otherwise specified in a case where there are multiple substances corresponding to the components in the composition. "Physiological saline" refers to a 0.9 mass % sodium chloride aqueous solution. "Room temperature" means 25° C.±2° C.

[Water-Absorbing Resin Particles]

The water-absorbing resin particles according to the present embodiment contain an imidazoline compound represented by Formula (1) below (hereinafter also simply referred to as an "imidazoline compound").

[Chem. 2]

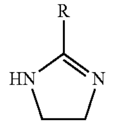

(1)

[In Formula (1), R represents a C1-3 alkyl group.]

Due to the imidazoline compound being incorporated, the water-absorbing resin particles according to the present embodiment have better water absorbency under no pressure and suppress reduction in viscosity over time when swollen with an iron-containing aqueous solution. Examples of iron-containing aqueous solutions include human urine, blood, or solutions (for example, medical waste liquids) containing one of these.

Water absorbency under no pressure can be evaluated by measuring a 5-minute value of non-pressurization DW. The 5-minute value of non-pressurization DW is a volume [mL/g] (volume per 1.00 g of water-absorbing resin particles) of physiological saline absorbed by the water-absorbing resin particles by 5 minutes after the start of absorption when the physiological saline is absorbed in 1.00 g of the water-absorbing resin particles through a non-pressurization DW method. The non-pressurization DW method is a water absorption test in which water-absorbing resin particles are placed on a liquid-permeable sheet (mesh sheet) placed on a measurement table with a through-hole and physiological saline supplied from the through-hole without pressure is absorbed by the water-absorbing resin particles. The inner diameter of the through-hole is usually 2 mm. The amount of water-absorbing resin particles to be tested is 1.00 t 0.01 g, and this amount of water-absorbing resin particles is uniformly distributed in a circular area with a diameter of 30 mm centered on the position directly above the through-hole. The measurement of a static water absorption rate through the non-pressurization DW method is performed in an environment of a temperature of 25° C. and a humidity of 60±10%. Other details of the test conditions will be described in examples described below.

The 5-minute value of non-pressurization DW of the water-absorbing resin particles according to the present embodiment may be 27 mL/g or more, 30 mL/g or more, or 33 mL/g or more, and may be 60 mL/g or less, 55 mL/g or less, 50 mL/g or less, 45 mL/g or less, or 40 mL/g or less.

The reduction in viscosity over time when swollen with an iron-containing aqueous solution can be evaluated through measuring the viscosity retention rate of a swollen gel formed by swelling the water-absorbing resin particles with iron-containing physiological saline. The viscosity retention rate of the swollen gel is calculated as a ratio (Y/X×100) of the viscosity of the swollen gel left for 5 hours after the formation of the swollen gel (hereinafter also referred to as "a 5-hour value (Y) of the swollen gel viscosity) to the viscosity of the swollen gel left for 1 hour after the formation of the swollen gel (hereinafter also referred to as "a 1-hour value (X) of the swollen gel viscosity"). The iron-containing physiological saline used for the formation of the swollen gel is physiological saline containing 50 mass ppm of iron ions based on the total mass of the iron-containing physiological saline. The swollen gel is formed using 34 times the amount of iron-containing physiological saline to the solid content of the water-absorbing resin particles. The swollen gel is allowed to stand in a hot air dryer at 40° C. The swollen gel viscosity is measured using a type-B viscometer under a temperature condition of 25° C. Other details of the test conditions will be described in examples described below.

The viscosity retention rate of the swollen gel obtained by swelling the water-absorbing resin particles with the iron-containing physiological saline may be 42% or higher, 45% or higher, 48% or higher, 50% or higher, or 55% or higher, and may be 60% or lower, 65% or lower, 70% or lower, 75% or lower, 80% or lower, or 100% or lower. The 1-hour value (X) of the swollen gel viscosity may be 18,000 mPa·s or more, 19,000 mPa·s or more, or 20,000 mPa s or more, and may be 25,000 mPa·s or less or 22,500 mPa·s or less. The 5-hour value (Y) of the swollen gel viscosity may be 8,200 mPa·s or more, 9,000 mPa s or more, 9,500 mPa s or more, or 9,900 mPa s or more, and may be 15,000 mPa·s or less or 13,000 mPa s or less.

The centrifuge retention capacity (CRC) of the water-absorbing resin particles may be 25 g/g or more or 30 g/g or more, and may be 60 g/g or less, 55 g/g or less, 50 g/g or less, 45 g/g or less, 40 g/g or less, or 35 g/g or less. The CRC is measured through a method described in the examples to be described below with reference to the EDANA method (NWSP 241.0.R2(15), pages 769-778).

The water content of the water-absorbing resin particles may be, for example, 15 mass % or less, 10 mass % or less, 5 mass % or less, 3 mass % or less, or 2.5 mass % or less based on the total mass of the water-absorbing resin particles. The water content based on the total mass of the water-absorbing resin particles is measured through a method described in the examples to be described below.

The water-absorbing resin particles may have a size to pass through a JIS standard sieve with openings of 850 μm.

The median particle diameter of the water-absorbing resin particles (or polymer particles) may be 150 to 800 μm, 150 to 700 μm, 200 to 600 μm, or 250 to 500 μm. The median particle diameter can be measured through the following method. The JIS standard sieves are combined in order from the top: a sieve with openings of 850 μm, a sieve with openings of 600 μm, a sieve with openings of 500 μm, a sieve with openings of 425 μm, a sieve with openings of 300 μm, a sieve with openings of 250 μm, a sieve with openings of 150 μm, and a saucer. 50 g of the water-absorbing resin particles was added to the combined uppermost sieve and classified according to JIS Z 8815 (1994) using a Ro-Tap Shaker (manufactured by Iida-Seisakusho Japan Corporation). After classification, the mass of particles remaining on each sieve is calculated as a mass percentage with respect to the total amount of particles to obtain particle size distribution. For this particle size distribution, the sieve top is accumulated in descending order of particle size, and the relationship between the sieve openings and the combined value of the mass percentages of the particles remaining on the sieves is plotted on logarithmic probability paper. By connecting the plots on the probability paper with a straight line, the particle diameter corresponding to 50 mass % of the cumulative mass percentages is obtained as a median particle diameter.

The shape of the water-absorbing resin particles (or polymer particles) is not particularly limited, and may be, for example, substantially spherical, crushed, or granular, and particles may be formed through agglomeration of primary particles having these shapes.

<Polymer Particles>

The water-absorbing resin particles usually contain polymer particles. Polymer particles may be water-absorbing particles containing polymers containing ethylenically unsaturated monomers as monomer units. Ethylenically unsaturated monomers may be water-soluble monomers, and examples thereof include (meth)acrylic acid and salts thereof, 2-(meth)acrylamide-2-methylpropanesulfonic acid and salts thereof, (meth)acrylamide, N,N-dimethyl(meth) acrylamide, 2-hydroxyethyl (meth)acrylate, N-methylol (meth)acrylamide, polyethylene glycol mono(meth)acrylate, N,N-diethylaminoethyl (meth)acrylate, N,N-diethylaminopropyl (meth)acrylate, and diethylaminopropyl (meth)acrylate. Ethylenically unsaturated monomers may be used alone or in combination of two or more thereof. The proportion of a polymer containing an ethylenically unsaturated monomer as a monomer unit in polymer particles is 50 to 100 mol %, 60 to 100 mol %, 70 to 100 mol %, or 80 to 100 mol % based on the total molar amount of the monomer constituting the polymer particles. The polymer particles may be particles containing (meth)acrylic acid polymers containing at least one of (meth)acrylic acid or (meth)acrylate as a monomer unit. The proportion of a monomer unit derived from (meth) acrylic acid or (meth)acrylate in a (meth)acrylic acid polymer may be 90 to 100 mol % based on the total molar amount of the monomer constituting the polymer.

The polymer particles may be surface crosslinked using a surface crosslinking agent. At least the polymers in the surface layer portion of the polymer particles may be crosslinked through a reaction with a surface crosslinking agent. The surface crosslinking agent may be, for example, a compound having two or more functional groups (reactive functional groups) having reactivity with functional groups derived from ethylenically unsaturated monomers. Examples of surface crosslinking agents include alkylene carbonate compounds such as ethylene carbonate and propylene carbonate; polyols such as 1,4-butanediol, diethylene glycol, triethylene glycol, propylene glycol, trimethylolpropane, glycerol, polyoxyethylene glycol, polyoxypropylene glycol, and polyglycerol; polyglycidyl compounds such as (poly)ethylene glycol diglycidyl ether, (poly)glycerol diglycidyl ether, (poly)glycerol triglycidyl ether, (poly)propylene glycol polyglycidyl ether, and (poly)glycerol polyglycidyl ether; haloepoxy compounds such as epichlorohydrin, epibromhydrin, α-methyl epichlorohydrin; compounds having two or more reactive functional groups such as isocyanate compounds such as 2,4-tolylene diisocyanate and hexamethylene diisocyanate; oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol; oxazoline compounds such as 1,2-ethylenebisoxazoline; and hydroxyalkylamide compounds such as bis[N,N-di(β-hydroxyethyl)]adipamide. The surface crosslinking agent may contain an alkylene carbonate compound. In a case where two types of surface crosslinking agents are used in combination, the proportion of an alkylene carbonate compound in the surface crosslinking agents may be 15 to 95 mass %, 20 to 80 mass %, 25 to 60 mass %, or 30 to 45 mass % based on the total mass of the surface crosslinking agents. The proportion of a polyol compound in the surface crosslinking agents may be 30 to 100 mass %, 40 to 90 mass %, 50 to 80 mass %, or 55 to 70 mass % based on the total mass of the surface crosslinking agents.

Also within the polymer particles, the polymers may be self-crosslinkable, crosslinked through a reaction with an internal crosslinking agent, or internally crosslinked through both the methods.

The internal crosslinking agent may contain, for example, a compound having two or more polymerizable unsaturated groups, a compound having two or more kinds of reactive functional groups having reactivity with functional groups of ethylenically unsaturated monomers, or a combination of one or more kinds of compounds.

Examples of compounds having two or more polymerizable unsaturated groups include di- or tri(meth)acrylic acid esters of polyols such as (poly)ethylene glycol (in the present specification, "polyethylene glycol" and "ethylene glycol" are collectively referred to as "(poly)ethylene glycol, and the same applies hereinafter), (poly)propylene glycol, trimethylolpropane, glycerol polyoxyethylene glycol, polyoxypropylene glycol, and (poly)glycerol; unsaturated polyesters obtained by reacting the above-described polyols with unsaturated acids such as maleic acid and fumaric acid; bisacrylamides such as N,N'-methylenebis(meth)acrylamide; di- or tri(meth)acrylic esters obtained by reacting polyepoxide with (meth)acrylic acid; di(meth) acrylic acid carbamyl esters obtained by reacting hydroxyethyl (meth) acrylate with polyisocyanates such as tolylene diisocyanate or hexamethylene diisocyanate; allylated starch; allylated cellulose; diallyl phthalate; N,N',N"-triallyl isocyanurate; and divinylbenzene.

Examples of compounds having two or more reactive functional groups include glycidyl group-containing compounds such as (poly)ethylene glycol diglycidyl ether, (poly) propylene glycol diglycidyl ether, and (poly)glycerol diglycidyl ether; (poly)ethylene glycol; (poly)propylene glycol; (poly)glycerol; pentaerythritol, ethylenediamine, polyethylene imine; and glycidyl (meth)acrylate.

The polymer particles may contain water to some extent in addition to the polymers of the ethylenically unsaturated monomers.

<Imidazoline Compound>

An imidazoline compound is a compound consisting of an imidazoline ring and a C1-3 alkyl group bound to the 2-position of the imidazoline ring. Since the imidazoline compound does not have a strong odor, the water-absorbing resin particles containing the imidazoline compound can be suitably used for sanitary materials. One embodiment of the water-absorbing resin particles containing the imidazoline compound can exhibit the above-described effect of the present invention without generating an odor, for example.

The water-absorbing resin particles may contain an imidazoline compound inside the polymer particles or an imidazoline compound attached to the surface of the polymer particles. In the case where an imidazoline compound is contained in the polymer particles, reduction in viscosity over time when swollen with an iron-containing aqueous solution can be further suppressed.

R in Formula (1) is a C1-3 alkyl group. The number of carbon atoms in the alkyl group as R may be 2 to 3 or 3 from the viewpoint that, for example, the effect of the present invention is more significantly exhibited. Examples of R include a methyl group, an ethyl group, an n-propyl group, and an isopropyl group. R may be a C3 alkyl group. Examples of imidazoline compounds include 2-(2-imidazoline-2-yl)propane and 2-propyl-2-imidazoline. One type of imidazoline compound may be contained, or a combination of two or more types thereof may be contained.

The content of imidazoline compound may be 25 mass ppm or more, 30 mass ppm or more, 35 mass ppm or more, 40 mass ppm or more, 50 mass ppm or more, 60 mass ppm or more, 70 mass ppm or more, 80 mass ppm or more, 90 mass ppm or more, 100 mass ppm or more, 150 mass ppm or more, or 200 mass ppm or more based on the solid content of the water-absorbing resin particles from the viewpoint of suppressing reduction in viscosity over time when swollen with an iron-containing aqueous solution, which is further enhanced by the effect of the present invention. The content of the imidazoline compound may be 11,000 mass ppm or less, 9,000 mass ppm or less, 7,000 mass ppm or less, 5,000 mass ppm or less, 3,000 mass ppm or less, 1,000 mass ppm or less, 800 mass ppm or less, 600 mass ppm or less, 400 mass ppm or less, or 300 mass ppm or less from the viewpoints of, for example, less gel blocking during liquid absorption and superior water absorbency under no pressure. From the viewpoint of superior water absorbency under no pressure, the content of the imidazoline compound may be 25 to 11,000 mass ppm, 25 to 5,000 mass ppm, 25 to 1,000 mass ppm, 25 to 800 mass ppm, 25 to 600 mass ppm, 25 to 400 mass ppm, or 25 to 200 mass ppm based on the solid content of the water-absorbing resin particles.

The content of imidazoline compound in the water-absorbing resin particles based on the solid content of the water-absorbing resin particles is measured through the method described in examples to be described below.

<Method for Producing Water-Absorbing Resin Particles>

The water-absorbing resin particles according to the present embodiment can be produced through a method including incorporating an imidazoline compound into the water-absorbing resin particles.

(Method for Producing Polymer Particles)

Polymer particles can be obtained, for example, through a method including a step of polymerizing monomers including ethylenically unsaturated monomers. The method for polymerizing monomers can be selected from, for example, a reversed-phase suspension polymerization method, an aqueous solution polymerization method, a bulk polymerization method, and a precipitation polymerization method. Internally crosslinked polymer particles may be obtained by polymerizing ethylenically unsaturated monomers in the presence of an internal crosslinking agent. Polymer particles internally containing inorganic particles such as silica may also be obtained by polymerizing ethylenically unsaturated monomers in the presence of the inorganic particles. Some or all of ethylenically unsaturated monomers may form salts such as alkali metal salts.

In the case of the aqueous solution polymerization method, polymer particles can be obtained through a method including: polymerizing ethylenically unsaturated monomers in a monomer aqueous solution containing the ethylenically unsaturated monomers and water to form a hydrogel polymer containing a polymer; and drying the hydrogel polymer. In a case where lumpy hydrogel polymer is formed, it may be coarsely crushed and the coarsely crushed hydrogel polymer may be dried. The hydrogel polymer or the coarsely crushed product thereof may be pulverized after drying, and particles obtained through the pulverization may be classified. The polymer particles may be dried, coarsely crushed products, or may be particles obtained by further pulverizing the coarsely crushed products. The polymer particles obtained through pulverizing the coarsely crushed products may be classified, and the particle size of the polymer particles may be adjusted as necessary.

The concentration of ethylenically unsaturated monomers in a monomer aqueous solution may be 20 mass % or more and below a saturated concentration, 25 to 70 mass %, or 30 to 50 mass % based on the mass of the monomer aqueous solution.

The monomer aqueous solution may further contain a polymerization initiator. The polymerization initiator may be a photopolymerization initiator or a thermal radical polymerization initiator or may be a water-soluble thermal radical polymerization initiator. The thermal radical polymerizable compound may be an azo compound, peroxide, or a combination thereof. The amount of polymerization initiator may be 0.01 to 15 millimoles based on 1 mole of ethylenically unsaturated monomer.

Examples of persulfates used as polymerization initiators include potassium persulfate, ammonium persulfate, and sodium persulfate. Examples of azo compounds used as polymerization initiators include 2,2'-azobis (2-amidinopropane) dihydrochloride, 2,2'-azobis[2-(N-phenylamidino) propane] dihydrochloride, 2,2'-azobis {2-[N-(4-chlorophenyl)amidino]propane} dihydrochloride, 2,2'-azobis {2-[N-(4-hydroxyphenyl)amidino]propane} dihydrochloride, 2,2'-azobis[2-(N-benzylamidino)propane] dihydrochloride, and 2,2'-azobis[2-(N-allylamidino)propane] dihydrochloride.

The monomer aqueous solution may further contain the above-described internal crosslinking agent. The amount of internal crosslinking agent may be, based on 1 mole of ethylenically unsaturated monomer, 0 millimoles or more, 0.001 millimoles or more, 0.01 millimoles or more, 0.015 millimoles or more, or 0.020 millimoles or more, and 2 millimoles or less, 1 millimole or less, 0.5 millimoles or less, or 0.1 millimoles or less. The monomer aqueous solution may further contain other additives such as a chain transfer agent and a thickener as necessary.

The polymerization temperature varies depending on the polymerization initiator used, but may be 0° C. to 130° C. or 10° C. to 110° C. The polymerization time may be 1 to 200 minutes or 5 to 100 minutes.

The water content of a hydrogel polymer formed through polymerization (the content of water based on the mass of the hydrogel polymer) may be 30 to 80 mass %, 40 to 75 mass %, or 50 to 70 mass %.

In a case of coarsely crushing a lumpy hydrogel polymer, the coarsely crushed product obtained through coarse crushing may be in the form of particles or may have an elongated shape such as a series of particles. The minimum width of the coarsely crushed product may be, for example, about 0.1 to 15 mm or 1.0 to 10 mm. The maximum width of the coarsely crushed product may be about 0.1 to 200 mm or 1.0 to 150 mm. Examples of devices for coarse crushing include kneaders (for example, a pressure kneader and a twin-arm kneader), meat choppers, cutter mills, and Pharma Mill. The lumpy hydrogel polymer may be cut before coarse crushing as necessary.

The hydrogel polymer or the coarsely crushed product thereof is dried to mainly remove water. The drying method may be a general method such as natural drying, heat drying, or vacuum drying. Polymer particles having a moderate particle size can be obtained by further pulverizing the dried hydrogel polymer or the coarsely crushed product thereof and classifying the obtained particles as necessary. The pulverization method is not particularly limited, and methods in which roller mills (roll mills), stamp mills, jet mills, high-speed rotary pulverizers (such as hammer mills, pin mills, and rotor beater mills), or container-driven mills (such as rotary mills, vibration mills, and planetary mills) are used are applicable, for example. The classification method is also not particularly limited, and methods in which vibration sieves, rotary shifters, cylindrical agitation sieves, blower shifters, or ro-tap shakers are used are applicable, for example.

The polymer particles produced through the above-described methods may be surface crosslinked using a surface crosslinking agent. For example, the surface crosslinked polymer particles can be produced through a method including surface crosslinking polymer particles by heating a reaction mixture containing polymer particles with a crosslinking agent solution containing water and a surface crosslinking agent.

The crosslinking agent solution may be a solution containing water and a surface crosslinking agent dissolved in water. The solvent contained in the crosslinking agent solution may be substantially only water. The proportion of the solvent other than water may be 25 mass % or less, 10 mass % or less, 5 mass % or less, or 1 mass % or less based on the mass of the crosslinking agent solution.

The amount of the surface crosslinking agent may be 0.01 to 40 millimoles, 0.1 to 30 millimoles, or 1 to 20 millimoles per mole of a monomer unit constituting a polymer in polymer particles.

The heating temperature and heating time for surface crosslinking are adjusted in consideration of the types of surface crosslinking agent so that a crosslinking reaction proceeds appropriately. For example, the heating temperature for surface crosslinking may be 80° C. or higher, 100° C. or higher, 120° C. or higher, 150° C. or higher, or higher than 180° C., and may be 190° C. or higher. The heating temperature for surface crosslinking may be 250° C. or lower. The heating time for surface crosslinking may be, for example, 5 to 90 minutes.

The surface crosslinked polymer particles may also be dried and classified as necessary.

The method for incorporating an imidazoline compound into water-absorbing resin particles is not particularly limited. For example, an imidazoline compound may be incorporated into water-absorbing resin particles through a method including heating a mixture containing polymer particles (for example, surface crosslinked polymer particles) and a compound solution containing water and an imidazoline compound. The obtained water-absorbing resin particles may also be dried and classified as necessary.

The compound solution may be a solution containing water and an imidazoline compound dissolved in water. The solvent contained in the compound solution may be substantially only water. The proportion of the solvent other than water may be 25 mass % or less, 10 mass % or less, 5 mass % or less, or 1 mass % or less based on the mass of the compound solution.

The heating temperature for incorporating an imidazoline compound may be 80° C. or higher, 100° C. or higher, 120° C. or higher, 150° C. or higher, or 180° C. or higher, and may be 250° C. or lower. The heating time for incorporating an imidazoline compound may be, for example, 5 to 90 minutes.

An imidazoline compound may be incorporated into water-absorbing resin particles through a method including mixing an imidazoline compound with a raw material (for example, a monomer aqueous solution) for producing polymer particles. When an imidazoline compound is mixed with a raw material of polymer particles, there is a tendency for water-absorbing resin particles containing the imidazoline compound inside the polymer particles to be likely to be obtained. Mixing of the imidazoline compound may be performed, for example, before, during, or after a polymerization reaction of a monomer.

The imidazoline compound can also be incorporated into water-absorbing resin particles through a method for incorporating a precursor compound of the imidazoline compound into a raw material of polymer particles. As the precursor compound, a compound capable of forming an imidazoline compound after the reaction can be used.

(Absorbent Article)

FIG. 1 is a cross-sectional view illustrating an example of an absorbent article. An absorbent article 100 shown in FIG. 1 includes a sheet-like absorbing body 10, core wraps 20*a* and 20*b*, a liquid permeable sheet 30, and a liquid impermeable sheet 40. In the absorbent article 100, the liquid impermeable sheet 40, the core wrap 20*b*, the absorbing body 10, the core wrap 20*a*, and the liquid permeable sheet 30 are layered in this order. In FIG. 1, there is a portion where there is a gap between members, but the members may be in close contact with each other without the gap.

The absorbing body 10 includes water-absorbing resin particles 10*a* according to the above-described embodiment, and a fiber layer 10*b* containing a fibrous material. The water-absorbing resin particles 10*a* are dispersed in the fiber layer 10*b*.

The core wrap 20*a* is placed on one surface side of the absorbing body 10 (on the upper side of the absorbing body 10 in FIG. 1) while being in contact with the absorbing body 10. The core wrap 20*b* is placed on the other surface side of the absorbing body 10 (on the lower side of the absorbing body 10 in FIG. 1) while being in contact with the absorbing body 10. The absorbing body 10 is placed between the core wrap 20*a* and the core wrap 20*b*. Examples of core wraps 20*a* and 20*b* include tissues and non-woven fabrics. The core wrap 20*a* and the core wrap 20*b* have, for example, main surfaces having the same size as that of the absorbing body 10.

The liquid permeable sheet 30 is placed on the outermost side into which a liquid to be absorbed infiltrates. The liquid permeable sheet 30 is placed on the core wrap 20*a* while being in contact with the core wrap 20*a*. Examples of the liquid permeable sheet 30 include porous sheets and non-woven fabrics made of synthetic resins such as polyethylene, polypropylene, polyesters, or polyamides. The liquid impermeable sheet 40 is placed on the outermost side of the absorbent article 100 opposite to the liquid permeable sheet 30. The liquid impermeable sheet 40 is placed on the lower side of the core wrap 20*b* while being in contact with the core wrap 20*b*. Examples of the liquid impermeable sheet 40 include sheets made of synthetic resins such as polyethylene, polypropylene, or polyvinyl chloride and sheets made of composite materials of these synthetic resins and non-woven fabrics. The liquid permeable sheet 30 and the liquid impermeable sheet 40 have a main surface wider than that of, for example, the absorbing body 10, and outer edge portions of the liquid permeable sheet 30 and the liquid impermeable sheet 40 extend around the absorbing body 10 and the core wraps 20*a* and 20*b*.

The size relationship between the absorbing body 10, the core wraps 20*a* and 20*b*, the liquid permeable sheet 30, and the liquid impermeable sheet 40 is not particularly limited, and is appropriately adjusted according to the use or the like of an absorbent article. In addition, the method for retaining the shape of the absorbing body 10 using the core wraps 20*a* and 20*b* is not particularly limited. An absorbing body may be wrapped with a plurality of core wraps as shown in FIG. 1 or may be wrapped with one sheet of core wrap.

Due to the imidazoline compound being incorporated, the water-absorbing resin particles according to the present embodiment have better water absorbency under no pressure and suppress reduction in viscosity over time when swollen with an iron-containing aqueous solution. As one embodiment of the present invention, there is provided a water absorption enhancer for water-absorbing resin particles under no pressure in which an imidazoline compound is incorporated as an active component. As another embodiment of the present invention, there is provided an agent for suppressing reduction in viscosity over time when water-absorbing resin particles, which contain an imidazoline compound as an active component, are swollen with an iron-containing aqueous solution. As still another embodiment of the present invention, there is provided: a method for incorporating an imidazoline compound into water-absorbing resin particles and improving water absorbency for water-absorbing resin particles under no pressure; a method for suppressing reduction in viscosity over time when water-absorbing resin particles are swollen with an iron-containing physiological saline; or a method for improving water absorbency of water-absorbing resin particles under no pressure and suppressing reduction in viscosity over time when the water-absorbing resin particles are swollen with an iron-containing aqueous solution.

EXAMPLES

Hereinafter, the contents of the present invention will be described in more detail with reference to examples and comparative examples, but the present invention is not limited to the following examples.

Production Example 1: Preparation of Surface Crosslinked Polymer Particles

Preparation of Partially Neutralized Acrylic Acid Solution 475.65 g (6.60 mol) of acrylic acid was added to a round-bottom cylindrical separable flask which is equipped with a stirrer and has an inner diameter of 11 cm and an internal volume of 2 L. After adding 395.70 g of ion-exchanged water into the separable flask while stirring this acrylic acid, 415.65 g of 48 mass % sodium hydroxide was added dropwise in an ice bath to prepare 1287.00 g of a partially neutralized sodium acrylate solution with a monomer concentration of 45 mass % (neutralization rate of 76 mol %).

Polymerization Step 231.91 g of ion-exchanged water and 1.32 g of polyethylene glycol diacrylate (NOF Corporation, BLEMMER ADE-400A) were added to 1253.30 g of the partially neutralized sodium acrylate solution having a monomer concentration of 45 mass % prepared above to obtain a reaction solution (monomer aqueous solution). Next, the above-described reaction solution was supplied to a jacketed 3 L stainless steel twin-arm kneader which has two sigma-type blades with a lid that could be opened and closed and is equipped with a thermometer and a nitrogen blowing tube, and the system was replaced with nitrogen gas for 1 hour while keeping the temperature of the reaction solution at 25° C. Subsequently, when 17.26 g (3.19 millimoles) of a 5.0 mass % potassium persulfate aqueous solution and 4.83 g of a 0.5 mass % L-ascorbic acid aqueous solution were added thereto while stirring the reaction solution, the temperature started to rise about 1 minute later and polymerization started. After 8 minutes, the maximum temperature during the polymerization reached 75° C., and then stirring was continued while keeping the jacket temperature at 60° C., and a hydrogel was taken out after 60 minutes from the initiation of the polymerization. The obtained hydrogel was sequentially put into a meat chopper 12VR-750SDX manufactured by Alpha Royal Co., Ltd. and segmented. The diameter of holes in a plate located at an outlet of the meat chopper was 6.4 mm.

[Drying and Pulverizing Step]

The coarsely crushed product thus obtained was laid out on a wire net with openings of 0.8 cm×0.8 cm and dried through hot air drying at 180° C. for 30 minutes to obtain a dried product. The dried product was pulverized using a centrifugal pulverizer (manufactured by Retsch GmbH, ZM200, screen diameter of 1 mm, 6000 rpm). The powder obtained through the pulverization was sieved by shaking for 1 minute using a sieve with openings of 850 μm and a sieve with openings of 180 μm. By classification, polymer particles (A) were collected as fractions that had passed through the 850 μm sieve but had not passed through the 180 μm sieve.

[Surface Crosslinking Step]

30 g of the polymer particles (A) was weighed into a round-bottom cylindrical separable flask which is equipped with a fluororesin anchor-type stirring blade and has an inner diameter of 11 cm. Next, while stirring at 300 rpm, a surface crosslinking agent solution obtained by mixing 0.094 g of ethylene carbonate, 0.150 g of propylene glycol, and 0.600 g of deionized water with each other was added dropwise to the separable flask using a Pasteur pipette and stirred for 5 minutes to obtain a mixture. This mixture was heated at 200° C. for 35 minutes. After cooling to room temperature, the mixture was classified with a sieve with openings of 850 μm. By classification, particles that had passed through the sieve with openings of 850 μm were obtained as surface cross-linked polymer particles (hereinafter also referred to as "material particles (A)"). This operation was repeated 10 times to obtain a required amount of material particles (A).

Example 1

20 g of the material particles (A) was weighed into a round-bottom cylindrical separable flask which is equipped with a fluororesin anchor-type stirring blade and has an inner diameter of 11 cm. Next, while stirring at 300 rpm, a 2-propyl-2-imidazoline aqueous solution obtained by mixing 0.197 g of 2-propyl-2-imidazoline (Tokyo Chemical Industry Co., Ltd.) with 0.400 g of deionized water was added dropwise to the separable flask using a Pasteur pipette and stirred for 5 minutes to obtain a mixture. This mixture was heated at 180° C. for 30 minutes. After cooling to room temperature, the mixture was classified with a sieve with openings of 850 μm. By classification, water-absorbing resin particles that had passed through the 850 μm sieve were obtained as water-absorbing resin particles of Example 1. At this time, it was found that 2-propyl-2-imidazoline was contained in an amount of 860 mass ppm with respect to the solid content of the water-absorbing resin particles from a result of quantitative analysis through GC-MS.

Example 2

20 g of the material particles (A) was weighed into a round-bottom cylindrical separable flask which is equipped with a fluororesin anchor-type stirring blade and has an inner diameter of 11 cm. Next, while stirring at 300 rpm, a 2-propyl-2-imidazoline aqueous solution obtained by mixing 0.029 g of 2-propyl-2-imidazoline (Tokyo Chemical Industry Co., Ltd.) with 0.400 g of deionized water was added dropwise to the separable flask using a Pasteur pipette and stirred for 5 minutes to obtain a mixture. This mixture was heated at 180° C. for 30 minutes. After cooling to room temperature, the mixture was classified with a sieve with openings of 850 μm. By classification, water-absorbing resin particles that had passed through the 850 μm sieve were obtained as water-absorbing resin particles of Example 2. At this time, it was found that 2-propyl-2-imidazoline was contained in an amount of 174 mass ppm with respect to the solid content of the water-absorbing resin particles from a result of quantitative analysis through GC-MS.

Example 3

20 g of the material particles (A) was weighed into a round-bottom cylindrical separable flask which is equipped with a fluororesin anchor-type stirring blade and has an inner diameter of 11 cm. Next, while stirring at 300 rpm, a 2-propyl-2-imidazoline aqueous solution obtained by mixing 0.005 g of 2-propyl-2-imidazoline (Tokyo Chemical Industry Co., Ltd.) with 0.400 g of deionized water was added dropwise to the separable flask using a Pasteur pipette and stirred for 5 minutes to obtain a mixture. This mixture was heated at 180° C. for 30 minutes. After cooling to room temperature, the mixture was classified with a sieve with openings of 850 μm. By classification, water-absorbing resin particles that had passed through the 850 μm sieve were obtained as water-absorbing resin particles of Example 3. At this time, it was found that 2-propyl-2-imidazoline was contained in an amount of 31 mass ppm with respect to the solid content of the water-absorbing resin particles from a result of quantitative analysis through GC-MS.

Comparative Example 1

20 g of the material particles (A) was weighed into a round-bottom cylindrical separable flask which is equipped with a fluororesin anchor-type stirring blade and has an inner diameter of 11 cm. Next, while stirring at 300 rpm, 0.400 g of deionized water was added dropwise to the separable flask using a Pasteur pipette and stirred for 5 minutes to obtain a mixture. This mixture was heated at 180° C. for 30 minutes. After cooling to room temperature, the mixture was classified with a sieve with openings of 850 μm. By classification, water-absorbing resin particles that had passed through the 850 μm sieve were obtained as water-absorbing resin particles of Comparative Example 1.

Example 4

Preparation of Partially Neutralized Acrylic Acid Solution 475.65 g (6.60 mol) of acrylic acid was added to a round-bottom cylindrical separable flask which is equipped with a stirrer and has an inner diameter of 11 cm and an internal volume of 2 L. After adding 395.70 g of ion-exchanged water into the separable flask while stirring this acrylic acid, 415.65 g of 48 mass % sodium hydroxide was added dropwise in an ice bath to prepare 1287.00 g of a partially neutralized acrylic acid solution with a monomer concentration of 46 mass % (neutralization rate of 76 mol %).

Polymerization Step 252.86 g of the prepared partially neutralized sodium acrylate solution, 39.65 g of ion-exchanged water, 0.27 g of polyethylene glycol diacrylate as an internal crosslinking agent (NOF Corporation, BLEMMER ADE-400A), and 0.17 g of 2-propyl-2-imidazoline (Tokyo Chemical Industry Co., Ltd.) were placed in a fluororesin-coated stainless vat (inner dimensions of its opening: 175 mm×130 mm, inner dimensions of its bottom surface: 155×110 mm, height: 30 mm). One stirrer (8 mm in diameter, 45 mm in length, without a ring) was installed in the central portion of the stainless vat, and a uniform liquid-like mixture (monomer aqueous solution) was formed through stirring. A thermometer for measuring the temperature of the mixture was installed in the central portion of the stainless vat. Thereafter, the opening of the stainless vat was covered with a polyethylene film. After adjusting the temperature of the mixture to 25° C., nitrogen gas was bubbled through a tube inserted into the mixture to replace the reaction system with nitrogen until the amount of dissolved oxygen became 0.1 ppm or less. Next, while stirring the mixture at 300 rpm, the tube for nitrogen replacement was removed from the reaction system, and 8.71 g (0.644 millimoles) of an potassium persulfate aqueous solution with a concentration of 2 mass % and 0.98 g of L-ascorbic acid aqueous solution with a concentration of 0.5 mass % were added dropwise to the mixture in the stainless vat using a syringe (3 mL disposable syringe manufactured by Henke Sass Wolf, injection needle manufactured by Terumo Corporation).

Immediately after the L-ascorbic acid aqueous solution was added dropwise thereto, a polymerization reaction started. Stirring was stopped 3 minutes after the completion of the dropwise addition of the L-ascorbic acid aqueous solution. After the viscosity of the reaction solution was increased with the progress of the polymerization reaction, the mixture gelled. The thermometer for measuring the temperature of the mixture indicated a maximum value of 73° C. 9 minutes after the completion of the dropwise addition of the L-ascorbic acid aqueous solution. Thereafter, the stainless vat in which the hydrogel polymer which contains water and a polymer and formed through gelation of the reaction solution was placed was immersed in a water bath at 75° C., and the hydrogel polymer was aged for 20 minutes in that state.

The hydrogel polymer which was the gelled mixture was taken out from the stainless vat and immediately cut into about 5 cm in width. The cut hydrogel polymer was coarsely crushed with a meat chopper (manufactured by Alpha Royal Co., Ltd., 12VR-750SDX).

The coarsely crushed product containing an elongated structure of the hydrogel polymer was discharged from the plurality of circular discharge holes of the plate attached to an end portion of a kneading chamber of the meat chopper. The diameter of the discharge holes was 6.4 mm. The coarse crushing with the meat chopper was continued for 5 minutes after the hydrogel polymer was added. The obtained coarsely crushed product was an aggregate formed of a plurality of elongated structures with a width of 4 to 6 mm.

Drying and Pulverizing Step

The coarsely crushed product thus obtained was laid out on a wire net with openings of 0.8 cm×0.8 cm and dried through hot air drying at 180° C. for 30 minutes to obtain a dried product. The dried product was pulverized using a centrifugal pulverizer (manufactured by Retsch GmbH, ZM200, screen diameter of 1 mm, 6000 rpm). The powder obtained through the pulverization was sieved by shaking for 1 minute using a sieve with openings of 850 μm and a sieve with openings of 180 μm. By classification, polymer particles (B) were collected as fractions that had passed through the 850 μm sieve but had not passed through the 180 μm sieve.

Surface Crosslinking Step 30 g of the polymer particles (B) was weighed into a round-bottom cylindrical separable flask which is equipped with a fluororesin anchor-type stirring blade and has an inner diameter of 11 cm. Next, while stirring at 300 rpm, a surface crosslinking agent solution obtained by mixing 0.094 g of ethylene carbonate, 0.150 g of propylene glycol, and 0.600 g of deionized water with each other was added dropwise to the separable flask using a Pasteur pipette and stirred for 5 minutes to obtain a mixture. This mixture was heated at 200° C. for 35 minutes. After cooling to room temperature, the mixture was classified with a sieve with openings of 850 μm. By classification, water-absorbing resin particles that had passed through the sieve with openings of 850 μm were obtained as water-absorbing resin particles of Example 4. At this time, it was found that 2-propyl-2-imidazoline was contained in an amount of 37 mass ppm with respect to the solid content from a result of quantitative analysis through GC-MS.

<Water Content>

2.0 g of water-absorbing resin particles is added to an aluminum foil case (No. 8) which is set to have a constant weight (W1 (*g*)) in advance, the opening of the aluminum foil case is lightly closed, and the total mass W2 (*g*) of the sample-containing aluminum foil case is accurately weighed out. The above-described sample-containing aluminum foil case is dried for 2 hours with a hot air dryer (manufactured by ADVANTEC, model: FV-320) of which internal temperature is set to 200° C. The sample-containing aluminum foil case after drying is allowed to cool to room temperature in a desiccator. The total mass W3 (*g*) of the sample-containing aluminum foil case after allowing to cool is measured. The water content of the sample was calculated by the following equation.

$$\text{Water content[mass \%]}=[\{(W2-W1)-(W3-WJ)\}/(W2-W1)]\times 100$$

<Centrifuge Retention Capacity>

The centrifuge retention capacity (CRC) was measured through the following procedure with reference to the EDANA method (NWSP 241.0.R2(15), pages 769-778). The measurement was performed in an environment of a temperature of 25° C.±2° C. and a humidity of 50%±10%.

A non-woven fabric (product name: Heat Pack MWA-18, manufactured by Nippon Paper Papylia Co., Ltd.) with a size of 60 mm×170 mm was folded in half in the longitudinal direction to adjust the size to 60 mm×85 mm. A 60 mm×85 mm non-woven fabric bag was manufactured by press-bonding the non-woven fabrics on both sides extending in the longitudinal direction through heat-sealing (press-bonded portions with a width of 5 mm were formed on both sides along the longitudinal direction). 0.2 g of water-absorbing resin particles was accurately weighed out and placed in the non-woven fabric bag. Thereafter, the non-woven fabric bag was closed by press-bonding the remaining one side extending in the transverse direction through heat-sealing.

The entire non-woven fabric bag was completely wetted by floating the non-woven fabric bag on 1,000 g of physiological saline contained in a stainless steel vat (240 mm×320 mm×45 mm) without folding the non-woven fabric bag. 1 Minute after the non-woven fabric bag was placed in the physiological saline, the non-woven fabric bag was immersed in the physiological saline with a spatula to obtain a non-woven fabric bag containing a gel.

30 minutes after the non-woven fabric bag was placed in the physiological saline (a total of 1 minute of the floating time and 29 minutes of immersion time), the non-woven fabric bag was taken out of the physiological saline. Then, the non-woven fabric bag was placed in a centrifuge (manufactured by Kokusan Co., Ltd., model number: H-122). After the centrifugal force of the centrifuge reached 250 G, the non-woven fabric bag was dehydrated for 3 minutes. After dehydration, the mass Ma[g] of the non-woven fabric bag including the mass of the gel was weighed. The same operation as described above was performed on the non-woven fabric bag without placing the water-absorbing resin particles, and the mass Mb[g] of the dehydrated non-woven fabric bag was measured. CRC [g/g] was calculated based on the following equation. Mc[g] is a value obtained by accurately weighing out the mass 0.2 g of the water-absorbing resin particles used for the measurement.

$$CRC=[(Ma-Mb)-Mc]/Mc$$

<Non-Pressurization DW>

Figure 2:
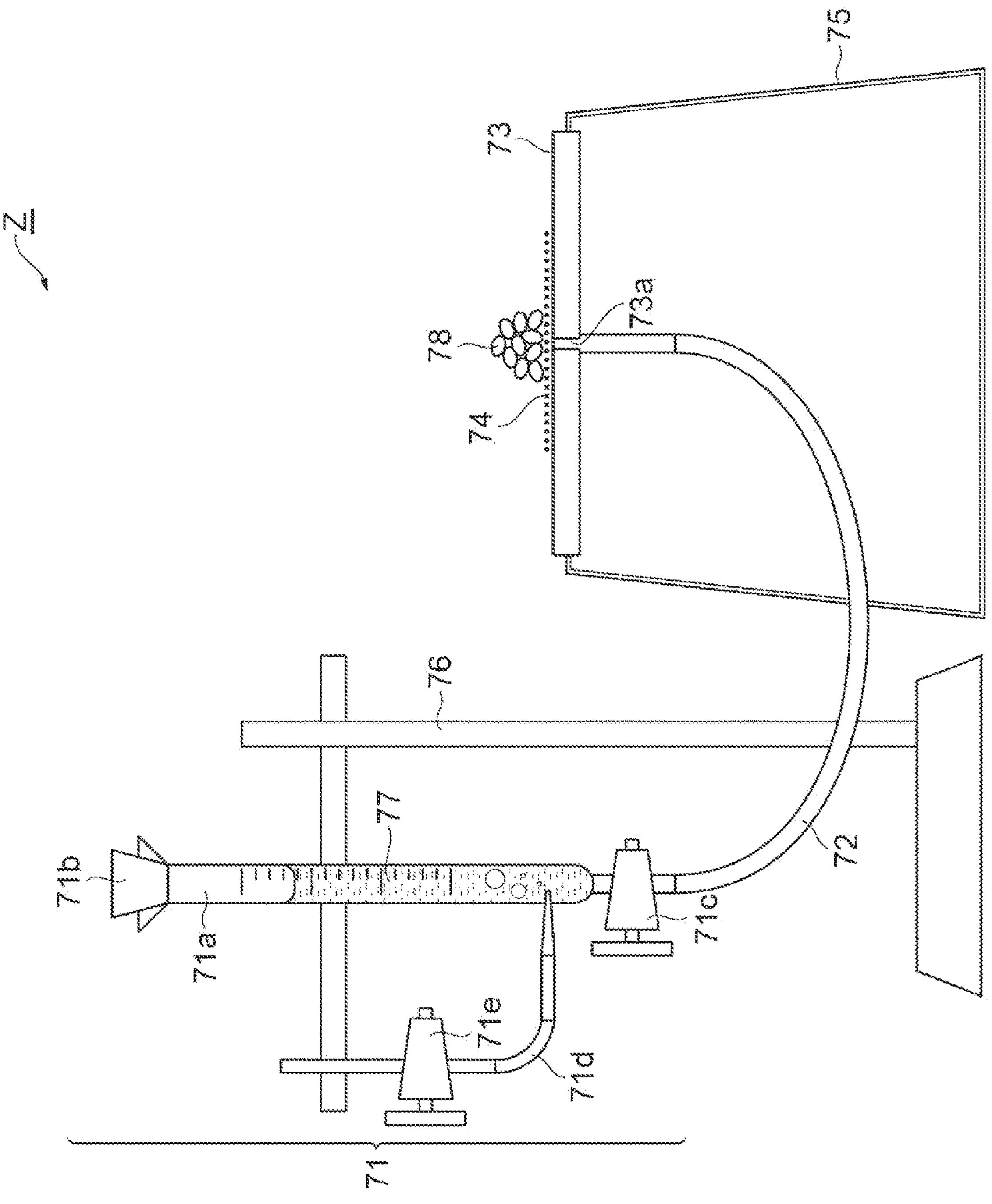
FIG. 2 is a schematic diagram illustrating a device for measuring non-pressurization DW of water-absorbing resin particles.

The non-pressurization DW of the water-absorbing resin particles was measured using a measurement device Z shown in FIG. 2. The particles to be measured are fractions of water-absorbing resin particles which have passed through a sieve with openings of 500 μm but have not been passed through a sieve with openings of 250 μm.

The measurement device Z has a burette portion 71, a conduit 72, a flat plate-shaped measurement table 73, a nylon mesh 74, a pedestal 75, and a clamp 76. The burette portion 71 has a burette 71*a* with a scale, a rubber stopper 71*b* sealing an opening in the upper portion of the burette 71*a*, a cock 71*c* connected to a distal end in the lower portion of the burette 71*a*, an air introduction tube 71*d* connected to the lower portion of the burette 71*a*, and a cock 71*e*. The burette portion 71 is fixed with the clamp 76. The measurement table 73 has a through-hole 73*a* with a diameter of 2 mm formed in its center portion and is supported by the pedestal 75 whose height is variable. The through-hole 73*a* of the measurement table 73 is connected to the cock 71*c* of the burette portion 71 via the conduit 72. The inner diameter of the conduit 72 is 6 mm.

The measurement was performed in an environment of a temperature of 25° C. and a humidity of 60%±10%. First, the cocks 71*c* and 71*e* of the burette portion 71 were closed, and a physiological saline 77 adjusted to 25° C. was added to the burette 71*a* through the opening in the upper portion of the burette 71*a*. After sealing the opening of the burette 71*a* with the rubber stopper 71*b*, the cocks 71*c* and 71*e* were opened. The inside of the conduit 72 was filled with the physiological saline 77 so as not to introduce air bubbles. The height of the measurement table 73 was adjusted so that the height of the surface of the physiological saline 77 reaching the inside of the through-hole 73*a* was the same as the height of the upper surface of the measurement table 73. At this time, it was confirmed that the same volume of air as that of the physiological saline 77 sucked out from the through-hole 73*a* was rapidly supplied into the burette via the air introduction tube 71*d*. After the adjustment, the height of the surface of the physiological saline 77 in the burette 71*a* was read on the scale of the burette 71*a*, and the position was taken as a zero point (read value at 0 seconds).

The nylon mesh 74 (100 mm×100 mm, 250 mesh, thickness: about 50 μm) was laid near the through-hole 73*a* on the measurement table 73, and a cylinder with an inner diameter of 30 mm and a height of 20 mm was placed in the center of the nylon mesh. 1.00 g of particles 78 to be measured was uniformly dispersed in the cylinder. Thereafter, the cylinder was carefully removed to obtain a sample in which the particles 78 to be measured were circularly dispersed in the center portion of the nylon mesh 74. Next, the nylon mesh 74 on which the particles 78 to be measured were placed was moved so quickly that the center of the nylon mesh was positioned at the through-hole 73*a* and the particles 78 to be measured did not dissipate, and the measurement was started. The time when air bubbles in the burette 71*a* were first introduced from the air introduction tube 71*d* was defined as a start of water absorption (0 seconds).

The amount of decrease in the physiological saline 77 in the burette 71*a* (that is, the amount of physiological saline 77 absorbed by the particles 78 to be measured) was sequentially read in units of 0.1 mL, and the decreased amount We[g] of the physiological saline 77 after 5 minutes counted from the start of the absorption of the particles 78 to be measured was read. From Wc, the 5-minute value of the non-pressurization DW was obtained by the following equation. The non-pressurization DW is the amount of water absorbed per 1.00 g of the particles 78 to be measured.

$$\text{Non-pressurization } DW \text{ value[mL/g]}=Wc/1.00$$

[Evaluation of Viscosity of Swollen Gel Prepared with Iron-Containing Aqueous Solution]

The viscosity of a swollen gel with an iron-containing aqueous solution was evaluated by measuring the viscosity of the swollen gel with an iron-containing physiological saline. The viscosity of the swollen gel for the water-absorbing resin particles obtained in the examples and the comparative example was evaluated through the following method.

Preparation of Iron-Containing Physiological Saline

Iron-containing physiological saline (with an iron ion concentration of 50 mass ppm) with the following composition was prepared.

Sodium chloride: 9.0 g
Ferrous sulfate heptahydrate: 0.249 g
Ion-exchanged water: 990.75 g Preparation of Swollen Gel with Iron-Containing Physiological Saline A swollen gel was prepared using 34 times the amount of iron-containing physiological saline to the solid content of water-absorbing resin particles.

97.14 g of the above-described iron-containing physiological saline solution was weighed into a tall beaker with an internal volume of 100 mL (manufactured by Sibata Scientific Technology Ltd., body outer diameter of 50 mm, height of 88 mm), and a magnetic stirrer bar (6 mm ϕ×20 mm without a ring) was placed on a magnetic stirrer (manufactured by Iuchi: HS-30D). Subsequently, the magnetic stirrer bar was adjusted to rotate at 600 rotations/minute. Next, 2.93 g of water-absorbing resin particles (water content: 2.3%, solid content: 2.86 g) was placed in a stirring beaker, the stirring was continued until rotating vortexes disappeared and the liquid level became horizontal, and a swollen gel was prepared as a measurement sample. Immediately after preparing the swollen gel, the stirrer tip was gently removed from the beaker, and the beaker containing the swollen gel was covered with plastic wrap (manufactured by Mitsubishi Chemical Corporation, DIA-WRAP).

(Evaluation of Viscosity of Swollen Gel)

Thereafter, the swollen gel was allowed to stand in a hot air dryer at 40° C. for 1 hour, the viscosity of the swollen gel was measured with a type-B viscometer (manufactured by Shibaura System, Vismetron VDH2 viscometer, rotational speed: 20 rpm, rotor: No. 6, timer: 60 sec.), and the value at this time was defined as a 1-hour value[mPa·s] of the swollen gel viscosity. The measurement was performed in an environment of a temperature of 25° C. The gel viscosity was measured three times, and an average value thereof was used.

Thereafter, the swollen gel was further allowed to stand in a hot air dryer at 40° C. for 4 hours, the viscosity of the swollen gel was measured in the same manner as above, and the value at this time was defined as a 5-hour value[mPa·s] of the swollen gel viscosity. The measurement was performed in an environment of a temperature of 25° C. The gel viscosity was measured three times, and an average value thereof was used.

[Calculation of Viscosity Retention Rate of Swollen Gel]

The viscosity retention rate[%] of the swollen gel was calculated by the following equation.

$$\text{Viscosity retention rate[\%] of swollen gel}=\text{5-hour value of swollen gel viscosity[mPa·s]}/\text{1-hour value of swollen gel viscosity[mPa·s]}\times 100$$

[Quantitative Analysis of 2-Propyl-2-Imidazoline Contained in Water-Absorbing Resin Particles Using GC-NPD and GC-MS Analyzers]

Quantitative analysis of 2-propyl-2-imidazoline contained in the water-absorbing resin particles was performed through the following method to obtain the content of imidazoline compound [mass ppm] in 1 g of the water-absorbing resin particles.

After adding 5 mL of distilled water to 1 g of the water-absorbing resin particles to swell the particles, 25 mL of acetone was added thereto to precipitate polymers. The obtained acetone solubles were collected in an eggplant flask while being filtered with filter paper, and concentrated with an evaporator. Thereafter, the concentrated liquid was transferred to a 10 mL volumetric flask, and the inside of the eggplant flask was rinsed with acetone to make a constant volume, and the liquid was subjected to GC-NPD measurement and GC/MS measurement.

GC-NPD and GC-MS analysis was carried out under conditions as follows. The content of imidazoline compound was calculated using a calibration curve prepared using 2-propyl-2-imidazoline (Tokyo Chemical Industry Co., Ltd.).

Analyzer: GC-NPD and GC-MS, Agilent Technologies, 7890A/5975C
Column: DB-Heavy Wax 30 m×0.25 mmID×0.25 μm
Carrier gas: He (3.0 mL/min)
Column temperature: 40° C. (3 min)→20° C./min→250° C.
Injection port: Split (5:1)
Injection port temperature: 250° C.
Detector: MS, NPD (selective detector for nitrogen and phosphorus compound)
Temperature: 300° C.
H2 flow rate: 3 mL/min
Air flow rate: 60 mL/min
Ionization method: EI
Emission current: 35 μA
Electron energy: 70 eV
E.M. Voltage: 1576 V
Source temperature: 230° C.
Q-Pole temperature: 150° C.
Interface temperature: 300° C.

[Calculation of Content of Imidazoline Compound with Respect to Solid Content of Water-Absorbing Resin Particles]

The content of imidazoline compound [mass ppm] with respect to the solid content of water-absorbing resin particles was obtained by the following equation.

$$\text{Imidazoline compound [mass ppm] with respect to solid content of water-absorbing resin particles}=(\text{content of imidazoline compound [mass ppm] in 1 g of water-absorbing resin particles})/(\text{solid content of water-absorbing resin particles [mass \%]})\times 100$$

$$\text{Solid fraction of water-absorbing resin particles [mass \%]}=100-\text{water content [mass \%]}$$

TABLE 1

| | | | | Evaluation of performance of water-absorbing resin particles | | | Viscosity of swollen gel prepared with iron-containing physiological saline | | |
|---|---|---|---|---|---|---|---|---|---|
| Example and comparative example | Additive | Method for producing water-absorbing resin particles | Content of imidazoline compound (mass ppm) | Water content (mass %) | CRC (g/g) | non-pressurization DW (mL/g) | 1-hour value (mPa · s) | 5-hour value (mPa · s) | Viscosity retention rate of swollen gel (1-hour value/ 5-hour vale) × 100 |
| Example 1 | 2-propyl-2-imidazoline | Production Example 1 | 860 | 2.3 | 33 | 29 | 19,050 | 9,750 | 51% |
| Example 2 | | | 174 | 2.1 | 32 | 34 | 19,200 | 9,750 | 51% |
| Example 3 | | | 31 | 1.6 | 33 | 33 | 19,850 | 9,950 | 50% |
| Comparative Example 1 | — | | 0 | 1.5 | 33 | 26 | 19,750 | 8,150 | 41% |
| Example 4 | 2-propyl-2-imidazoline | Production Example 2 | 37 | 1.7 | 33 | 35 | 22,050 | 12,550 | 57% |

Table 1 shows the measurement results of a 5-minute value of non-pressurization DW and a viscosity retention rate of each swollen gel. As shown in Table 1, it was confirmed that, by incorporating 2-propyl-2-imidazoline into water-absorbing resin particles, the water-absorbing resin particles have better water absorbency under no pressure and suppress reduction in viscosity over time when swollen with an iron-containing aqueous solution.

REFERENCE SIGNS LIST

10 Absorbing body
10*a* Water-absorbing resin particles
10*b* Fiber layer
20*a*, 20*b* Core wrap
30 Liquid permeable sheet
40 Liquid impermeable sheet
71 Burette portion
71*a* Burette
71*b* Rubber stopper
71*c*, 71*e* Cock
71*d* Air introduction tube
72 Conduit
73 Measurement table
74 Nylon mesh
73*a* Through-hole
75 Pedestal
76 Clamp
77 Physiological saline
78 Particles to be measured
100 Absorbent article
Z Measurement device

The invention claimed is:

1. Water-absorbing resin particles comprising:

an imidazoline compound represented by Formula (1) below, (1)

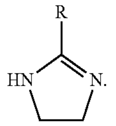

wherein in Formula (1), R represents a C1-3 alkyl group.

2. The water-absorbing resin particles according to claim 1, wherein the imidazoline compound has a content of 25 to 11,000 mass ppm based on a solid content of the water-absorbing resin particles.

3. The water-absorbing resin particles according to claim 1, wherein R is a C3 alkyl group.

4. An absorbing body comprising:

the water-absorbing resin particles according to claim 1.

5. An absorbent article comprising:

the absorbing body according to claim 4.

* * * * *